United States Patent
Li et al.

(10) Patent No.: US 10,982,253 B2
(45) Date of Patent: Apr. 20, 2021

(54) NUCLEIC ACID CATENANE WITH A LINKING DUPLEX BIOSENSOR FOR DETECTION OF A MICROORGANISM TARGET

(71) Applicant: McMaster University, Hamilton (CA)

(72) Inventors: Yingfu Li, Dundas (CA); John Brennan, Dundas (CA); Meng Liu, Dundas (CA)

(73) Assignee: McMaster University, Hamilton (CA)

( * ) Notice: Subject to any disclaimer, the term of this patent is extended or adjusted under 35 U.S.C. 154(b) by 358 days.

(21) Appl. No.: 16/060,649

(22) PCT Filed: Dec. 12, 2016

(86) PCT No.: PCT/CA2016/051459
§ 371 (c)(1),
(2) Date: Jun. 8, 2018

(87) PCT Pub. No.: WO2017/096492
PCT Pub. Date: Jun. 15, 2017

(65) Prior Publication Data
US 2018/0363022 A1    Dec. 20, 2018

Related U.S. Application Data

(60) Provisional application No. 62/266,207, filed on Dec. 11, 2015.

(51) Int. Cl.
*C12P 19/34* (2006.01)
*C12Q 1/04* (2006.01)
(Continued)

(52) U.S. Cl.
CPC ............. *C12Q 1/04* (2013.01); *C12Q 1/6806* (2013.01); *C12Q 1/686* (2013.01); *C12Q 2525/207* (2013.01); *C12Q 2525/307* (2013.01); *C12Q 2561/113* (2013.01); *C12Q 2600/158* (2013.01); *C12Q 2600/166* (2013.01); *C12Q 2600/178* (2013.01)

(58) Field of Classification Search
None
See application file for complete search history.

(56) References Cited

U.S. PATENT DOCUMENTS

| 2010/0028923 | A1* | 2/2010 | Walt ..................... C12Q 1/37 435/19 |
| 2016/0289750 | A1* | 10/2016 | Landegren ........... C12Q 1/6816 |
| 2019/0203277 | A1* | 7/2019 | Minev ................... C07H 21/00 |

OTHER PUBLICATIONS

Hu et al., Nano Letters 15, 2099-2103 (Feb. 2015). (Year: 2015).*
(Continued)

*Primary Examiner* — Kenneth R Horlick
(74) *Attorney, Agent, or Firm* — Melanie Szweras; BERESKIN & PARR LLP/ S.E.N.C.R.L., s.r.l.

(57) ABSTRACT

The present application is directed to biosensors and methods for detecting a microorganism target in a sample using a mechanically interlocked nucleic acid catenane, wherein an enzyme from the microorganism target or that is activated by a molecule from the microorganism target cleaves a linkage in a first single-stranded nucleic acid ring of the catenane structure, allowing rolling-circle amplification to occur and the presence of rolling-circle amplification products indicates the presence of the microorganism in the sample.

20 Claims, 16 Drawing Sheets
Specification includes a Sequence Listing.

(51) Int. Cl.
   *C12Q 1/6806* (2018.01)
   *C12Q 1/686* (2018.01)

(56) References Cited

OTHER PUBLICATIONS

International Search Report and Written Opinion of corresponding PCT Application No. PCT/CA2016/051459 dated Mar. 21, 2017.
Wang, F. et al., "From Cascaded Catalytic Nucleic Acids to Enzyme-DNA Nanostructures: Controlling Reactivity, Sensing, Logic Operations and Assembly of Complex Structures", Chemical Reviews, ASC Publications, Feb. 27, 2014, vol. 114, pp. 2881-2941.
Li, T. et al., "Interlocked DNA Nanostructures Controlled by a Reversible Logic Circuit", Nature Communications, Sep. 27, 2014, vol. 5, pp. 1-8.
Lei, Y. et al., "Microbial Biosensors", Analytica Chimica Acta, May 24, 2006, vol. 568, Issues 1-2, pp. 200-210.
Deisingh, A.K. et al. "Biosensors for the Detection of Bacteria", Can. J. Microbiol., published online on Feb. 6, 2004, vol. 50, pp. 69-77.
Liu, M. et al., "Programming a Topologically Constrained DNA Nanostructure into a Sensor", Nature Communications, Jun. 23, 2016, vol. 7, pp. 1-7.
Liu, M. et al., "Biosensing by Tandem Reactions of Structure Switching, Nucleolytic Digestion, and DNA Amplification of a DNA Assembly", Angew. Chem. Int. Ed., Jun. 2015, vol. 54, pp. 9637-9641.
Wu, Z. S. et al., "Engineering Interlocking DNA Rings with Weak Physical Interactions", Nat. Commun., Jun. 27, 2014, vol. 5, pp. 1-10.
Ali, M. M. et al., "Fluorogenic DNAzyme Probes as Bacterial Indicators", Angew. Chem. Int. Ed., Mar. 15, 2011, vol. 50, Issue 16, pp. 3751-3754.
Aguirre S. D. et al., "A Sensitive DNA Enzyme-based Fluorescent Assay for Bacterial Detection", Biomolecules, Aug. 30, 2013, vol. 3, pp. 563-577.
Fire, Andrew et al: "Rolling replication of short DNA circles", Proc. Natl. Acad. Sci., May 1995, vol. 92, pp. 4641-4645.
Jung, Cheulhee et al.: "Diagnostic Applications of Nucleic Acid Circuits", Accounts of Chemical Research; May 14, 2014; vol. 47, pp. 1825-1835.
Liu, Dongyu et al.: "Rolling Circle DNA Synthesis: Small Circular Oligonucleotides as Efficient Templates for DNA Polymerases", J. Am. Chem. Soc., Feb. 21, 1996; vol. 117, issue 7, pp. 1587-1594.
Niemz, Angelika et al.: "Point-of-care nucleic acid testing for infectious diseases", National Institute of Health, Trends Biotechnol., May 2011, vol. 29, Issue 5, pp. 240-250.
Zanoli, Laura Maria et al.: "Isothermal Amplification Methods for the Detection of Nucleic Acids in Microfluidic Devices", Biosensors, Mar. 2013, vol. 3, pp. 18-43.
Schmidt, T. L. & Heckel, A.: "Construction of a structurally defined double-stranded DNA catenane". Nano Lett., Mar. 2011, vol. 11, pp. 1739-1742.
Zhang, D. Y. & Seelig, G.: "Dynamic DNA nanotechnology using strand displacement reactions". Nat. Chem., Jan. 2011; vol. 3, pp. 103-113.

\* cited by examiner

NUCLEIC ACID CATENANE WITH A LINKING DUPLEX BIOSENSOR FOR DETECTION OF A MICROORGANISM TARGET

CROSS REFERENCE TO RELATED APPLICATIONS

This application is a National Stage of International Application No. PCT/CA2016/051459 filed on Dec. 12, 2016 which claims the benefit of priority from U.S. provisional patent application No. 62/266,207, filed Dec. 11, 2015, the contents of both of which are incorporated herein by reference.

INCORPORATION OF SEQUENCE LISTING

A computer readable form of the Sequence Listing "P50019US01_ST25_Sequence_Listing.txt" (4,764 bytes), submitted via EFS-WEB and created on Jan. 22, 2021, is herein incorporated by reference.

FIELD

The present application relates to a biosensor for detecting analytes, various kits and methods of use thereof. In particular, the biosensor's mode of operation is based on binding of analytes to an analyte-binding nucleic acid enzyme which triggers rolling circle amplification and detection of the amplified product as the indicator of the presence of the analyte.

BACKGROUND

DNA is not only important in biological systems as genetic material, it has also become a key player in synthetic biology. DNA can be engineered into catalysts (DNAzymes) and molecular receptors (DNA aptamers), making DNA a functionally versatile polymer. DNA, as a highly programmable material based on predictable Watson-Crick base-pairing interactions, has also become a valuable macromolecule for rational engineering of molecular machines for potential nanotechnology applications.

In recent years, tremendous progress has been made toward building DNA-based nanodevices with increasing structural complexity and functional capabilities [1-13]. One important feature of many reported DNA nanostructures, such as DNA Borromean rings [1] and DNA catenanes [3], is the use of mechanically interlocked topologies to connect individual DNA components. The mechanical interlocking between DNA strands can be easily achieved in the case of DNA through the formation of a linking duplex between partner rings before ring closure. The existence of a linking duplex is not only creates a strong connectivity between partner rings but also provides stability for these well-defined structures.

Many rationally engineered DNA nanostructures use mechanically interlocked topologies to connect individual DNA components. The physical connectivity of these structures is made possible through the formation of a strong linking DNA duplex. The existence of such a structural element also poses a significant topological constraint on the function of the component rings.

SUMMARY

The present application demonstrates that the strong physical engagement of two mechanically interlocked single-stranded DNA rings in a DNA [2] catenane (termed D2C) with a strong linking duplex makes the component rings unsuitable as templates for "rolling circle amplification (RCA)". The present application further demonstrates that the linking-duplex feature enables the use of topologically interlocked architectures, such as DNA catenanes, for the design of amplified biosensors for bioanalytical applications.

In one embodiment, when one of the component rings is engineered to be a substrate of a stimuli-responsive RNA-cleaving DNAzyme, the system can be programmed into a biosensor that is capable of reporting a target of interest in three sequential reactions: target-induced RNA cleavage, nucleolytic conversion of the cleavage product into a DNA primer, and DNA amplification via RCA.

Accordingly, the present application includes a biosensor for detection of a microorganism target comprising:
 a) a first single-stranded nucleic acid ring comprising a linkage that is cleaved by an enzyme from the microorganism target or by an enzyme that is activated by a molecule from the microorganism; and
 b) a second single-stranded nucleic acid ring comprising a sequence complementary to a region of the first single-stranded nucleic acid ring, wherein the first- and second-single stranded nucleic acid rings form a nucleic acid catenane structure with a linking duplex.

In another aspect of the present application there is included a method of detecting a microorganism in a sample comprising exposing the sample to the biosensor system of the application, wherein an enzyme from the microorganism target cleaves the linkage in the first single-stranded nucleic acid ring, allowing rolling-circle amplification to occur and the presence of rolling-circle amplification products indicates the presence of the microorganism in the sample.

This disclosure not only expands the range of potential applications of mechanically interlocked DNA architectures, but also features an amplified biosensing system with a very high level of detection sensitivity. Accordingly, in one aspect of the disclosure there is provided a method for detecting the model bacterial pathogen *Escherichia coli* at a detection limit of 10 cells/mL using a DNA catenane biosensor.

In further aspects, the present application includes a biosensor system for detection of a microorganism target comprised of:
 a) a DNA catenane with a linking duplex and containing a ribonucleotide linkage
 b) an allosteric DNAzyme that can cleave the ribonucleotide linkage in the presence of the micro-organism target In some embodiments, the DNA catenane of the biosensor system of the application is comprised of:
 a) a first single-stranded DNA ring with a single ribonucleotide linkage
 b) a second single-stranded DNA ring having a sequence complementary to a region of the first single-stranded DNA region
 c) the first- and second-single stranded DNA rings forming a DNA catenane structure with a linking duplex In further aspects, the present application also includes a method of detecting a microorganism in a sample comprising:
 exposing the sample to the biosensor system, wherein the allosteric DNAzyme interacts with the microorganism target and becomes activated and cleaves the ribonulceotide linkage in the DNA catenane, thereby allowing rolling-circle amplification to occur and the presence of rolling-circle amplification products indicating the presence of the microorganism in the sample.

In some embodiments, the detection of single stranded DNA molecules generated by rolling circle amplification is indicated by colour. In some embodiments, the detection of single stranded DNA molecules generated by rolling circle amplification also comprises the addition of polynucleotide kinase prior to rolling-circle amplification Other features and advantages of the present application will become apparent from the following detailed description. It should be understood, however, that the detailed description and the specific examples, while indicating embodiments of the application, are given by way of illustration only and the scope of the claims should not be limited by these embodiments, but should be given the broadest interpretation consistent with the description as a whole.

DRAWINGS

The embodiments of the application will now be described in greater detail with reference to the attached drawings in which:

FIG. 1 illustrates the inability of a D2C to undergo RCA. (a) schematic illustration of a D2C made of $^CDNA_i$ and $^CDNA_{ii}$, with a linking duplex of 24 base-pairs (BP); (b) Synthesis of D2C1 by circularizing linear $DNA_{ii}$ over $^CDNA_i$ as the template: Lane M-markers made of $^LDNA_{ii}$, $^CDNA$ and $^CDNA_{ii}$, Lane R-circularization mixture; (c) RCA reactions with gel-purified $^CDNA_i$, $^CDNA_{ii}$ and D2C1 using $DP_i$ and $DP_{ii}$ as primers, RP: RCA product, Lane L: DNA ladders ranging from 1-10 kilo base-pairs.

FIG. 2 illustrates exemplary RCA reactions with $^CDNA'_i$, $r^CDNA'_{ii}$ and rD2C1' using DP1 and DP2 as primers. (a) Sequence of rD2C1'. It contains a linking duplex of 9 base pairs (boxed nucleotides); in comparison, rD2C1 has a linking duplex of 24 base-pairs (see FIG. 1b). F: fluorescein-dT; R: adenosine ribonucleotide; Q: dabcyl-dT. (b) and (c) RCA reactions using DP1 and DP2 as primers, respectively. RP: RCA product. Lane L: DNA ladders ranging from 1-10 kilo base-pairs.

FIG. 3 illustrates the cleavage of an RNA containing D2C by an RCD in an exemplary embodiment of the application. (a) Restoration of RCA compatibility of an rD2C using an RCD. (b) Cleavage of rD2C1 by EC1, an E. coli-responsive DNAzyme. Concentration of E. coli: $10^5$ cells/mL. Reaction mixtures were analyzed by 10% denaturing PAGE. EC1M: a mutant EC1 that cannot be activated by E. coli. Both $r^CDNA_{ii}$ and $^CDNA_i$ in rD2C1 were radioactively labeled with $^{32}P$ to facilitate DNA visualization on gel. Clv %: percent cleavage.

FIG. 4 shows a schematic illustration of the activity of EC1, an exemplary E. coli-responsive DNAzyme. EC1 cleaves a chimeric DNA/RNA substrate at a lone RNA linkage (R) flanked by two nucleotides labeled with a fluorophore (F) and a quencher (Q), respectively, and the cleavage activity of EC1 is dependent on an undeciphered protein molecule (represented by the star) secreted specifically by E. coli. The DNAzyme works simply by incubating EC1 with the crude extracellular mixture of E. coli as it contains the targeted protein molecule.

FIG. 5 shows a 10% dPAGE analysis of cleaved products of rD2C1 generated upon incubation in the presence of EC1 and E. coli for different incubation times.

FIG. 6 illustrates the 3'-5' exonucleolytic activity of exemplary φ29DP on $r^CDNA_{ii}$ and rD2C1. Degradation of EC1 mediated cleavage product of $r^CDNA_{ii}$ (a and b) and rD2C1 (c) by φ29DP and PNK. Concentration of E. coli: $10^5$ cells/mL. Reaction mixtures were analyzed by 20% denaturing PAGE. SF: small DNA fragment; LF: large DNA fragment. M lanes contain various DNA markers as indicated. $r^CDNA_{ii}$, both $r^CDNA_{II}$ and $^CDNA_i$ in rD2C1 were radioactively labeled with $^{32}P$ to facilitate DNA visualization on gel.

FIG. 7 shows the degradation of $r^LDNA_{ii}$ by exemplary φ29DP. All the reactions were carried out at 30° C. in 20 μL of 1×RCA reaction buffer containing 250 nM $^LDNA_{ii}$ and 5 U φ29DP. The degradation products were analyzed by 20% dPAGE.

FIG. 8 shows the cleavage of rD2C1 by exemplary φ29DP at different digestion times in the absence or presence of EC1, E. coli, PNK or all components.

FIG. 9 shows the results of an exemplary E. coli-dependent RCA reaction. (a) RCA reactions of rD2C1 in the presence of E. coli ($10^5$ cells/mL) analyzed using 0.6% agarose gel electrophoresis. Note every reaction also contained PNK and dNTPs. RP: RCA product. L: DNA ladders ranging from 1-10 kilo base-pairs. (b) Determination of detection sensitivity through analysis of RP using 0.6% agarose gel electrophoresis. (c) Determination of detection sensitivity via the colorimetric assay enabled by PW17 peroxidase DNAzyme. (d) Analysis of assay specificity using the colorimetric assay. The gram-negative bacteria used were Serratia fonticola (SF), Achromobacter xylosoxidans (AX), Yersinia ruckeri (YR) and Hafnia alvei (HA). The gram-positive bacteria used were Leuconostoc mesenteroides (LM) and Pediococcus acidilactici (PA).

FIG. 10 shows the analysis of exemplary EcoRV-digested RCA products by 10% dPAGE.

FIG. 11 shows the exemplary RCA reactions of rD2C1 in the presence of E. coli ($10^4$ cells mL$^{-1}$) and small RNAs (5 ng, prepared from breast cancer cell line MCF-7) analyzed using (a) agarose gel electrophoresis and (b) colourimetric assay. RP: RCA product. L: DNA ladders ranging from 1-10 kilo base-pairs.

FIG. 12 shows the exemplary E. coli-dependent HRCA reaction. (a) schematic illustration of HRCA. FP1: forward primer; RP1: reverse primer. (b) Denaturing PAGE analysis of HRCA products. RP: RCA products; SA: secondary amplicons produced from the initial RCA products. (c) Real-time monitoring of HRCA reactions at various E. coli concentrations.

DETAILED DESCRIPTION

I. Definitions

Figure 1:
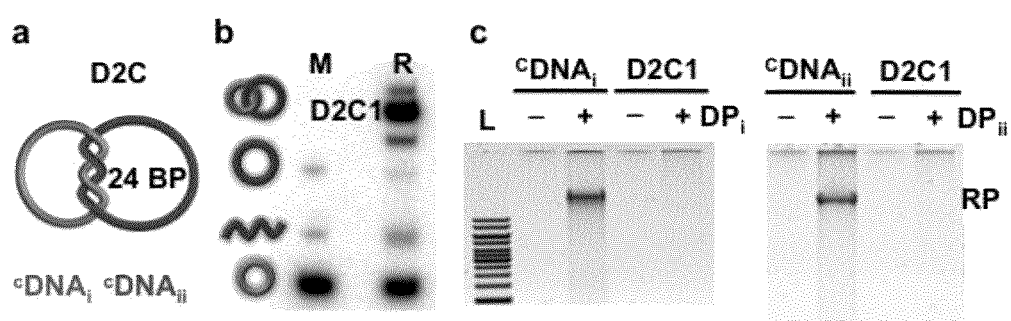

Unless otherwise indicated, the definitions and embodiments described in this and other sections are intended to be applicable to all embodiments and aspects of the present application herein described for which they are suitable as would be understood by a person skilled in the art.

As used herein in this specification and the appended claims, the singular forms "a", "an" and "the" include plural references unless the content clearly dictates otherwise. Thus for example, a composition containing "an analyte" includes one such analyte or a mixture of two or more analytes.

As used in this application and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used in this application and claim(s), the word "consisting" and its derivatives, are intended to be close ended terms that specify the presence of stated features, elements, components, groups, integers, and/or steps, and also exclude the presence of other unstated features, elements, components, groups, integers and/or steps.

The term "consisting essentially of", as used herein, is intended to specify the presence of the stated features, elements, components, groups, integers, and/or steps as well as those that do not materially affect the basic and novel characteristic(s) of these features, elements, components, groups, integers, and/or steps.

The terms "about", "substantially" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

The term "suitable" as used herein means that the selection of the particular compound or conditions would depend on the specific manipulation to be performed but the selection would be well within the skill of a person trained in the art.

The term "analyte" as used herein means any agent for which one would like to sense or detect using a biosensor of the present application. The term analyte also includes mixtures of compounds or agents such as, but not limited to, combinatorial libraries and samples from an organism or a natural environment.

The term "sample(s)" as used herein refers to any material that one wishes to assay using the biosensor of the application. The sample may be from any source, for example, any biological (for example human or animal medical samples), environmental (for example water or soil) or natural (for example plants) source, or from any manufactured or synthetic source (for example food or drinks). The sample is one that comprises or is suspected of comprising one or more analytes.

The term "nucleic acid" refers to polynucleotides such as deoxyribonucleic acid (DNA) and ribonucleic acid (RNA).

The term "rolling circle amplification" or "RCA" as used herein refers to a unidirectional nucleic acid replication that can rapidly synthesize multiple copies of circular molecules of DNA or RNA. In an embodiment, rolling circle amplification is an isothermal enzymatic process where a short DNA or RNA primer is amplified to form a long single-stranded DNA or RNA using a circular DNA template and an appropriate DNA or RNA polymerase. Further, the term "hyper-branched rolling circle amplification" or "HRCA" is a technique derived from rolling circle amplification to improve upon the sensitivity of RCA by using both forward and reverse primers. The forward primer produces a multimeric single-stranded DNA (ssDNA) or single-stranded RNA (ssRNA), which then becomes the template for multiple reverse primers. The DNA or RNA polymerase then extends the reverse primer during the extension process and the downstream DNA or RNA is displaced to generate branching or a ramified DNA or RNA complex. When all ssDNA and ssRNA strands have been converted into double-stranded DNA (dsDNA) or double-stranded RNA (dsRNA), the process ceases.

The term "exonucleolytic trimming" or "exonucleolytic digestion" as used herein refers to the cleaving of nucleotides one at a time from the end (exo) of a polynucleotide chain by a nucleic acid exonuclease.

The term "gel electrophoresis" or "electrophoresis system" as used herein refers to a technique to separate biological macromolecules including proteins or nucleic acids (nucleic acid electrophoresis), according to their electrophoretic mobility. The gel electrophoresis process can be performed under denaturing or non-denaturing conditions.

The term "nucleic acid" as used herein refers to a biopolymer made from monomers of nucleotides. Each nucleotide has three components: a 5-carbon sugar, a phosphate group and a nitrogenous base. If the sugar is deoxyribose, the biopolymenr is DNA (deoxyribonucleic acid). If the sugar is ribose, the biopolymer is RNA (ribonucleic acid). When all three components are combined, they form a nucleotide.

The term "oligonucleotide" as used herein refers to short single stranded DNA or RNA oligomers that are either synthetic or found in nature. Oligonucleotides are characterized by the sequence of nucleotide residues that make up the entire molecule. The length of the oligonucleotide is usually denoted by "-mer". For example, an oligonucleotide of six nucleotides (nt) is a hexamer, while one of 25 nt would usually be called a "25-mer". Oligonucleotides readily bind, in a sequence-specific manner, to their respective complementary oligonucleotides, DNA or RNA, to form duplexes.

The term "nucleic acid catenane" as used herein refers to a molecular structure comprising two or more mechanically interlocked marcrocyclic single stranded nucleic acid rings. The structure comprises a region of a linking duplex between partner rings to impart strong interconnectivity and stability to the structure.

The term "enzyme" as used herein refers to any molecule that accelerates or catalyzes the cleavage of the linkage in the first single-stranded nucleic acid ring. The term enzyme as used herein refers to all types of enzymes including protein enzymes, DNAzymes and ribozymes, including allosteric versions thereof.

The term "allosteric enzyme" as used herein refers to an enzyme for which activity is regulated by binding of an effector molecule at a site other than the enzyme's active site.

The term "sample(s)" as used herein refers to any material that one wishes to assay for the presence of the microorganism target using the biosensor of the application.

The term "reporter molecules for detection" as used herein refers to one or more molecules that are used to detect the presence of microorganism target.

The term "detection system" as used herein refers to any means that produces a signal that is detectable, for example, using colorimetric, fluorescent, electrochemical and/or radioimaging methods, when the microorganism target is present and RCA takes place.

II. Biosensors of the Application

The present application includes a biosensor for detection of a microorganism target comprising:
a) a first single-stranded nucleic acid ring comprising a linkage that is cleaved by an enzyme from the microorganism target or by an enzyme that is activated by a molecule from the microorganism; and
b) a second single-stranded nucleic acid ring comprising a sequence complementary to a region of the first single-stranded nucleic acid ring,
wherein the first- and second-single stranded nucleic acid rings form a nucleic acid catenane structure with a linking duplex.

In some embodiments, the linkage is cleaved by an RNA-cleaving DNAzyme, a DNA-cleaving DNA enzyme, a ribozyme or a protein enzyme that has DNA and/or RNA cleaving activities. In some embodiments, the linkage that is cleaved by the DNAzymes, ribozymes and protein enzymes is a ribonucleotide linkage. In some embodiments, the DNAzymes, ribozymes and protein enzymes are allosteric enzymes that are activated by an activator molecule from the microorganism target prior to cleaving the linkage.

In some embodiments the linkage is cleaved by an RNA-cleaving DNAzyme, a DNA-cleaving DNAzyme, a ribozyme or a protein enzyme that has DNA and/or RNA cleaving activities activated by a molecule from the microorganism target. In some embodiments, the linkage is cleaved by an RNA-cleaving DNAzyme that is activated by a molecule from the microorganism target. In some embodiments, the linkage is cleaved by an allosteric DNAzyme, ribozyme or protein enzyme that is activated by an activator molecule in a sample containing the microorganism target prior to cleaving the linkage.

In some embodiments, the biosensor further comprises the enzyme that is activated by a molecule from the microorganism.

In some embodiments, the microorganism target is a bacterium, virus or fungus. In some embodiments, the microorganism is a bacterium. In some embodiments, the bacterium is *E. coli*. In some embodiments, the microorganism is a virus.

In some embodiments, the first single stranded nucleic acid ring is a single stranded DNA ring comprising a ribonucleotide linkage and the second single-stranded nucleic acid ring is a single stranded DNA ring comprising a sequence that is complementary to a region of the first single-stranded DNA ring.

In some embodiments, the sequence in the first single stranded DNA ring that is complementary to a region of the first single-stranded DNA ring comprises from 6 to 50 nucleotides, from 10 to 40 nucleotides, from 20 to 30 nucleotides or 24 nucleotides.

Cleavage of the linkage results in release and linearization of first single-stranded nucleic acid. In some embodiments, this first single-stranded nucleic acid then acts as a primer for rolling circle amplification (RCA) to occur. Detection of RCA products (RP) indicates the presence of the microorganism. In some embodiments, the RCA utilizes the second single-stranded nucleic acid ring as the circular template and the linearized first single-stranded nucleic acid as the primer.

Cleavage of the linkage results in release and linearization of first single-stranded nucleic acid. In some embodiments, a DNA or RNA primer is then supplied to initiate rolling circle amplification (RCA). Detection of RCA products (RP) indicates the presence of the microorganism. In some embodiments, the RCA utilizes the second single-stranded nucleic acid ring as the circular template.

Accordingly, in some embodiments of the application the biosensor further comprises reagents for performing RCA. In some embodiments the reagents for performing RCA comprise one or more of a nucleic acid polymerase having exonuclease activity, RCA reaction buffer and nucleoside triphosphates (NTPs).

In some embodiments, the NTPs are ATP, GTP, UTP and CTP. In some embodiments, NTPs are deoxynucleoside triphosphates (dNTPs) selected from dATP, dGTP, dUTP and dCTP. In some embodiments, the NTPs are radiolabeled.

In some embodiments the nucleic acid polymerase is a DNA polymerase having 3' to 5' exonuclease activity or an RNA polymerase having 3' to 5' exonuclease activity. In some embodiments, the nucleic acid polymerase is a DNA polymerase. In some embodiments, the nucleic acid polymerase is phi29 DNA polymerase ɸ29DP).

In some embodiments, the reagents for performing RCA further comprise polynucleotide kinase (PNK). The PNK removes the terminal 2',3' cyclic phosphate in a ribonucleotide remaining after cleavage of the first single-stranded nucleic acid ring. In some embodiments, removal of the 2',3' cyclic phosphate allows the nucleic acid polymerase having exonuclease active to digest the linearized first single-stranded ring, removing nucleotides until a primer for the RCA is obtained.

In some embodiments, the reagents for performing RCA comprise a primer nucleic acid for performing RCA on the second single-stranded nucleic acid ring. In this embodiment, addition of PNK is not required as the linearized first single-stranded nucleic acid is not used as the RCA primer.

In some embodiments, the reagents for performing RCA comprise forward and reverse primers for performing hyperbranched RCA (HRCA).

In some embodiments the first and second nucleic acid rings are comprised of DNA, RNA or a mixture of DNA and RNA. In some embodiments, the first and second nucleic acid rings are comprised of DNA, with the first nucleic acid ring comprising a single ribonucleotide linkage.

In some embodiments, detection of the microorganism target is performed by detection of RCA products (RP) and the biosensor of the application further comprises one or more reporter molecules for detection of the RCA products (RP). In some embodiments, the one or more reporter molecules for detection of the RP comprise a detection system selected from a fluorescent system, a colorimetric system, a radiolabeled system and an electrochemical system. In some embodiments, the one or more reporter molecules are incorporated in the reagents for performing RCA and/or first and/or second single-stranded nucleic acid rings.

In some embodiments, a radiolabeled dNTP, such as an $[\alpha^{-32}P]dNTP$ is included in the reagents for performing RCA so that the RCA product (RP) becomes radioactive, and therefore detectable. In some embodiments, a fluorophore-labeled oligonucleotide that can hybridize with the RP is added to the reagents for performing RCA to produce a detectable fluorescence signal. In some embodiments, gold nanoparticles (AuNPs) functionalized with an oligonucleotide that is complementary to the RP used to produce a detectable colorimetric signal.

In some embodiments, the first single-stranded nucleic acid ring is modified to produces an RP containing repetitive units of a peroxidase-mimicking DNAzyme, such as PW17, generating a detectable colorimetric signal is used. In this embodiment, hemin, $H_2O_2$ and 2,2'azine-bis(3-ethylbenzthiasoline-6-sulfonic acid (ABTS) are included in the reagents for performing RCA. In the presence of hemin, PW17 catalyzes the $H_2O_2$-mediated oxidation of ABTS into a coloured product.

In some embodiments, the presence of the RP is detected using an electrophoresis system and the presence of the target nucleic acid is confirmed by detection of a single molecular weight band. The process of preparing the sample, preparing the gel and subsequent visualization techniques of the electrophoresis system are well known in the prior art.

In some embodiments, the biosensors of the application are comprised in a kit. Accordingly, the present application also includes a microorganism detection kit comprising a biosensor of the application. In some embodiments, the kit further comprises reagents for performing an assay using the biosensor of the application. In some embodiments, the kit further comprises instructions for using the biosensor in the assay and any controls needed to perform the assay.

In some embodiments, the reagents for performing an assay using the biosensor of the application include the first and second single stranded nucleic acid rings and one or more of an enzyme that is activated by a molecule from the microorganism, a RCA buffer, NTPs (such as dNTPs), nucleic acid polymerase (such as DNA polymerase, including φ29DP), PNK, ABST, $H_2O_2$, hemin, reagents for performing electrophoresis, reagents for performing fluorescence imaging, and reagents for performing positive and/or negative controls and assay grade solvents, such as water. In some embodiments, a primer for performing RCA on the second single stranded nucleic acid ring is also included in the reagents for performing the assay using the biosensor of the application.

The biosensor of the application advantageously provides enhanced detection sensitivity. In some embodiments, the detection sensitivity of the biosensor of the application is from about 10 cells/mL to about 1000 cells/ml, suitably as low as 10 cells/mL.

III. Methods of the Application

In another aspect of the present application there is included a method of detecting a microorganism target in a sample comprising exposing the sample to the biosensor system of the application, wherein an enzyme from the microorganism target, or an enzyme that is activated by a molecule from the microorganism target, cleaves the linkage in the first single-stranded nucleic acid ring, allowing rolling-circle amplification to occur and detection of rolling circle amplification products indicates the presence of the microorganism in the sample.

The sample may be from any source, for example, any biological (for example human or animal medical samples), environmental (for example water or soil) or natural (for example plants) source, or from any manufactured or synthetic source (for example food or drinks). The sample is one that comprises or is suspected of comprising one or more microorganism targets. In some embodiments, the sample is treated to concentrate the microorganism prior to application to the biosensor of the application.

In some embodiments, a cleavage reaction mixture is prepared by combining the sample, the nucleic acid catenane structure with a linking duplex and the enzyme that is activated by a molecule from the microorganism, in a buffer and the mixture incubated at about room temperature for about 30 minutes to about 90 minutes, or about 60 minutes. If the linearized first single-stranded nucleic acid is to serve as the RCA primer, then PNK is added to the reaction mixture and a further incubation at about 35° C. to about 40° C., or at about 37° C., is performed for about 10 minutes to about 50 minutes or about 30 minutes. If a separate primer is to be used for the RCA reaction, then the PNK addition step is omitted. In some embodiments, the RCA reaction is then initiated by addition of the nucleic acid polymerase, the NTPs, the primer (if using) and an RCA reaction buffer. In some embodiments, the RCA reaction mixtures are incubated at about 25° C. to about 30° C., or at about 30° C., for about 30 minutes to about 90 minutes, or about 60 minutes, before heating to about 80° C. to about 100° C., or at about 90° C., for about 3 minutes to about 10 minutes, or about 5 minutes.

EXAMPLES

The following non-limiting examples are illustrative of the present application:
Development of Biosensors Comprising a Nucleic Acid Assembly
Materials All DNA oligonucleotides (Table 1) were purchased from Integrated DNA Technologies (IDT) and purified by 10% denaturing (8 M urea) polyacrylamide gel electrophoresis (dPAGE). T4 polynucleotide kinase (PNK), T4 DNA ligase and φ29 DNA polymerase (φ29DP) were purchased from MBI Fermentas (Burlington, Canada). α-[$^{32}$P]ATP was purchased from PerkinElmer. All other chemicals were purchased from Sigma-Aldrich (Oakville, Canada) and used without further purification. The autoradiogram images of gels were obtained using a Typhoon 9200 variable mode imager (GE healthcare) and analyzed using Image Quant software (Molecular Dynamics).
Preparation of $^C$DNA$_i$ Phosphorylation of $^L$DNA$_i$. $^L$DNA$_i$ was first labeled with γ-[$^{32}$P]ATP at the 5' end using T4 polynucleotide kinase (PNK) according to the manufacturer's protocol. To ensure that all DNA molecules contained the 5' phosphate required for the subsequent ligation reaction, PNK mediated end-labeling solution containing 5'-$^{32}$P labeled $^L$DNA$_i$ was further incubated with 2 mM non-radioactive ATP at 37° C. for 30 min. The phosphorylated DNA was purified by 10% dPAGE.

Circularization of $^L$DNA$_i$. A total of 400 pmol of $^L$DNA$_i$ was first mixed with 450 pmol DNA$_i$CT in 50 μL of $H_2O$, followed by heating at 90° C. for 1 min. After cooling to room temperature and leaving the solution for 15 min, 10 μL of 10×T4 DNA ligase buffer (400 mM Tris-HCl, 100 mM $MgCl_2$, 100 mM DTT, 5 mM ATP, pH 7.8 at 25° C.) and 10 U of T4 DNA ligase were added (total 100 μL) and the mixtures were incubated at room temperature for 2 h. $^C$DNA$_i$ was concentrated by standard ethanol precipitation and purified by 10% dPAGE.
Preparation of r$^L$DNA$_{ii}$ and r$^C$DNA$_{ii}$ Synthesis of $^L$DNA$_{ii}$. r$^L$DNA$_{ii}$ was produced through T4 DNA ligase mediated ligation of FS28, DNA$_{ii}$F1 and DNA$_{ii}$F2 in the presence of DNA$_{ii}$T1 and DNA$_{ii}$T2 as ligation templates. A total of 400 pmol of FS28 was first mixed with 400 pmol of DNA$_{ii}$F2, 10 U of PNK and 5 mM ATP in 50 μL 1×PNK buffer (50 mM Tris-HCl, pH 7.6 at 25° C., 10 mM $MgCl_2$, 5 mM DTT, 0.1 mM spermidine). The mixture was incubated at 37° C. for 1 h, followed by heating at 90° C. for 1 min. Then 400 pmol of DNA$_{ii}$F1, 450 pmol of DNA$_{ii}$T1 and 450 pmol of DNA$_{ii}$T2 were added, heated at 90° C. for 40 s, cooled down to room temperature and left for 10 min. To the above mixture were added 15 μL of 10×T4 DNA ligase buffer (400 mM Tris-HCl, 100 mM MgCl$_2$, 100 mM DTT, 5 mM ATP, pH 7.8 at 25° C.) and 15 U of T4 DNA ligase, and the resultant mixture (total 150 µL) was incubated at room temperature for 2 h. The obtained r$^L$DNA$_{ii}$ was concentrated by standard ethanol precipitation and purified by 10% dPAGE.

Synthesis of r$^C$DNA$_{ii}$. A total of 300 pmol of r$^L$DNA$_{ii}$ was first phosphorylated using a similar protocol described above for the phosphorylation of $^L$DNA$_i$. The phosphorylated r$^L$DNA$_{ii}$ was mixed with 400 pmol of DNA$_{ii}$CT in 50 µL of H$_2$O, heated to 90° C. for 1 min, cooled to room temperature and left for 15 min. To this mixture were added 10 µL of 10×T4 DNA ligase buffer and 10 U of T4 DNA ligase, and the resultant mixture (total 100 µL) was incubated at room temperature for 2 h. The resultant r$^C$DNA$_{ii}$ was concentrated by ethanol precipitation and purified by 10% dPAGE.

Preparation of r$^L$-DNA'$_{ii}$ and r$^C$DNA'$_{ii}$.

Synthesis of r$^L$DNA'$_{ii}$. r$^L$DNA'$_{ii}$ was prepared using similar procedures described for r$^L$DNA$_{ii}$ except for the substitution of DNA$_{ii}$F2 with DNA'$_{ii}$F2.

Synthesis of r$^C$DNA'$_{ii}$. r$^C$DNA'$_{ii}$ was prepared using similar procedures described for r$^C$DNA$_{ii}$ except for the substitution of r$^L$-DNA$_{ii}$ and DNA$_{ii}$CT with r$^L$DNA'$_{ii}$ and DNA'$_{ii}$CT, respectively.

Preparation of rD2C1

A total of 100 pmol of $^L$DNA$_{ii}$ was first labeled with is γ-[$^{32}$P]ATP at the 5' end using T4 polynucleotide kinase (PNK) according to the manufacturer's protocol. To ensure that all DNA molecules contained the 5' phosphate required for the subsequent ligation reaction, PNK mediated end-labeling solution containing 5'-$^{32}$P labeled $^L$DNA$_{ii}$ was further incubated with 2 mM non-radioactive ATP at 37° C. for 30 min. 120 pmol of $^C$DNA$_1$ was added and heated to 90° C. for 30 s. After cooling to room temperature and leaving the solution for 15 min, 10 µL of 10×T4 DNA ligase buffer and 10 U T4 DNA ligase were added (total 100 µL) and incubated at room temperature for 2 h. The obtained rD2C1 molecules were concentrated by standard ethanol precipitation and purified by 10% dPAGE.

Preparation of rD2C1'

A total of 100 pmol of $^L$DNA'$_1$ was first phosphorylated by using PNK. Then 150 pmol of r$^C$DNA'$_{ii}$ was added and heated to 90° C. for 30 s. After cooling to room temperature and leaving the solution for 15 min, 200 pmol of DNA'$_i$CT was added and allowed to react for 30 min. To the above mixture were added 15 µL of 10×T4 DNA ligase buffer and 15 U of T4 DNA ligase, and the resultant mixture (total 150 µL) was incubated at room temperature for 2 h. The obtained rD2C1' molecules were concentrated by standard ethanol precipitation and purified by 10% dPAGE.

Methods

E. coli-Dependent RCA Reaction

A single colony of E. coli K12 freshly grown on a Luria Broth (LB) agar plate was taken and used to inoculate 2 mL of LB. After shaking at 37° C. for 14 h at 250 rpm, the bacterial culture was serially diluted in 10-fold intervals. 100 µL of each diluted solution was plated onto a LB agar plate (done in triplicate) and cultured at 37° C. for 15 h to obtain the cell counts. Colonies in each plate were counted; the average number of colonies from the three plates was taken as the number of E. coli cells for this dilution. This number was then used to calculate the number of cells for the other dilutions. 500 µL of each dilution was centrifuged at 13,000 g for 20 min at 4° C. and re-suspended in 100 µL of 1×RB (50 mM HEPES, 150 mM NaCl, 15 mM MgCl$_2$, pH 7.5). After being frozen at −20° C., E. coli cells were sonicated for 1 min and put on the ice for 5 min. This process was repeated three times. Then the cell suspension containing different numbers of E. coli cells were centrifuged at 13,000 g for 10 min at 4° C. The obtained crude intracellular mixture produced by the E. coli cells (CIM-EC) in the supernatant was used for the following experiment.

A cleavage reaction mixture containing 5 µL of CIM-EC, 1 µL of rD2C1 (5 µM), 4 µL of EC1 (50 µM) and 10 µL of 2×RB was incubated at RT for 60 min. Then 1 µL of PNK (10 U/µL) was added and incubated at 37° C. for 30 min. The RCA reaction was initiated by the addition of 1 µL of φ29DP (10 U/µL), 1 µL of dNTPs (50 mM), 5 µL of 10×RCA reaction buffer and 22 µL of water. The reaction mixtures were incubated at 30° C. for 60 min before heating at 90° C. for 5 min. The resultant RCA products were analyzed by 0.6% agarose gel electrophoresis.

Colorimetric Detection rD2C1 used for the colorimetric detection of E. coli was made of $^C$DNA$_{ii}$ and $^C$DNA$_i$CD. After the cleavage reaction described above, 1 µL of PNK (10 U/µL) was added and incubated at 37° C. for 30 min. The RCA reaction was then initiated by the addition of 1 µL of φ29DP (10 U/µL), 1 µL of dNTPs (50 mM), 2 µL of hemin (100 µM), 5 µL of 10×RCA reaction buffer and 20 µL of water. The reaction mixtures were incubated at 30° C. for 60 min before heating at 65° C. for 20 min. After cooling to RT, 2 µL of ABTS (50 mM) and 1 µL of H$_2$O$_2$ (8.8 mM) were added, and the colorimetric result was recorded immediately using a digital camera.

HRCA Reaction

Following the cleavage reaction, 1 µL of PNK (10 U/µL) was added and incubated at 37° C. for 30 min. The HRCA reaction was then initiated by the addition of 1 µL of φ29DP (10 U/µL), 1 µL of dNTPs (50 mM), 1 µL of FP1 (50 µM), 1 µL of RP1 (50 µM), 5 µL of 10×RCA reaction buffer, 2.5 µL of 20×EvaGreen and 17.5 µL of water. These reactions were carried out in BioRad CFX96 qPCR system set to a constant temperature of 30° C., and the fluorescence intensity was recorded in 1 min intervals.

Comparison of the Cleavage Activity of EC1 and EC1M in the Presence of E. coli.

E. coli K12 was grown onto a Luria Broth (LB) agar plate for 12 h at 37° C. A single colony was then taken and used to inoculate 2 mL of LB. After shaking at 37° C. for 14 h at 250 rpm, the bacterial culture was serially diluted in 10-fold intervals. One E. coli glycerol stock containing an average of 5000 colony forming units (CFUs) per 100 µL was inoculated into 2 mL of LB and grown at 37° C. for 6 h with shaking at 250 rpm. 1 mL of this culture was centrifuged at 13,000 g for 20 min at 4° C. The cell pellet was suspended in 200 µL of 1×RB (50 mM HEPES, 150 mM NaCl, 15 mM MgCl$_2$, pH 7.5). After being frozen at −20° C., E. coli cells were sonicated for 1 min and put on the ice for 5 min. This process was repeated three times. The cell suspension was then centrifuged at 13,000 g for 10 min at 4° C. The obtained supernatant was used as the CIM-EC for the experiment (CIM: Crude intracellular mixture; EC: E. coli).

The cleavage reaction with the CIM-EC was carried out by mixing 5 µL of CIM-EC, 1 µL of rD2C1 (5 µM), 4 µL of EC1 or EC1M (50 µM) and 10 µL of 2×RB. The above mixture was incubated at RT for 60 min, followed by 20% dPAGE analysis.

Degradation of rD2C1 by φ29DP in the Presence of EC1, E. coli and PNK.

A reaction mixture containing 5 µL of CIM-EC, 1 µL of rD2C1 (5 µM), 4 µL of EC1 (50 µM) and 10 µL of 2×RB was incubated at RT for 60 min. Then 1 µL of PNK (10 U µL$^{-1}$)

was added and incubated at 37° C. for 30 min. The digestion reaction was initiated by the addition of 1 µL of φ29DP (10 U µL$^{-1}$), 3 µL of 10×RCA reaction buffer and 5 µL of water. The reaction mixtures were incubated at 30° C. for 30 min before heating at 90° C. for 1 min, cooling to room temperature and 20% dPAGE analysis.

Cell Culture and miRNA Extraction.

The adherent breast cancer cell line MCF-7 was cultured in α-MEM media (GIBCO) supplemented with 10% fetal bovine serum (Invitrogen). These cells were cultured at 37° C. in a humidified atmosphere containing 5% $CO_2$. Small RNAs (<200 nt) were extracted and purified using the E.Z.N.A®miRNA Kit according to the manufacturer's protocol including 1) cell lysis, 2) organic extraction, 3) large RNA removal. The RNA quantity was determined by measuring optical density at 260 nm using the NanoVue™ Plus spectrophotometer.

Restriction Digestion of RCA Products.

A 2 µL portion of the RCA products (FIG. 4a) was mixed with 4 µL of 100 µM DT1 and heated at 90° C. for 5 min before cooled to RT and left for 20 min. This was followed by the addition of 1 µL of 10× Fast digestion buffer and 1 µL of FastDigestEcoRV. The reaction mixture was then incubated at 37° C. for 10 min and analyzed by 10% dPAGE.

Effect of Blood on RCA Reactions.

One milliliter of the human blood sample was first centrifuged at 13,000 g for 10 min at 4° C. to remove the plasma. After re-suspension in 1 mL of 50 mM HEPES buffer (containing 100 mM NaCl, 5 mM KCl, 1 mM $MgCl_2$ and 0.05% Tween 20), the sample was sonicated for 5 min to obtain blood cell suspension containing hemoglobin (a major PCR inhibitor). This sample was taken to set up five 50 µL RCA reactions made of 1 µL of $^C$DNA$_i$ (5 µM), 1 µL of DP1 (10 µM), 1 µL of φ29DP (10 U µL$^{-1}$), 1 µL of dNTPs (50 mM), 5 µL of 10×RCA reaction buffer, and 1, 2.5, 5, 10, and 25 µL of the blood cell suspension, supplemented with enough water to make up 50 µL. Each reaction was incubated at 37° C. for 30 min.

Detection of E. coli in Blood Samples

The whole human blood sample (Innovative Research) was drawn from a healthy person and treated by sodium citrate. Freshly cultured E. coli K12 cells were diluted and spiked in 1 mL of this blood sample. Then the sample was centrifuged at 13,000 g for 10 min at 4° C. to remove the plasma. After washing twice with 50 mM HEPES buffer (containing 100 mM NaCl, 5 mM KCl, 1 mM $MgCl_2$ and 0.05% Tween 20), the cell pellet was suspended in 500 µL of 1×RB, sonicated for 1 min, put on the ice for 5 min, and sonicated for another 2 min. The cell suspension was then centrifuged at 13,000 g for 10 min at 4° C. 10 µL of the obtained supernatant was then mixed with 1 µL of rD2C1 (5 µM), 4 µL of EC1 (50 µM) and 5 µL of 4×RB was incubated at RT for 60 min. Then 1 µL of PNK (10 U µL$^{-1}$), 1 µL of φ29DP (10 U µL$^{-1}$), 1 µL of dNTPs (50 mM), 1 µL of FP1 (50 µM), 1 µL of RP1 (50 µM), 5 µL of 10×RCA reaction buffer, 2.5 µL of 20× EvaGreen and 17.5 µL of water and 22 µL of water were added. These reactions were carried out in BioRad CFX96 qPCR system set to a constant temperature of 30° C., and the fluorescence intensity was recorded in 1 min intervals.

Detection of E. coli Using an ELISA Kit

CIM-EC samples from freshly cultured E. coli were prepared using similar procedures described above. The assay was performed according to the manufacturer's protocol.

Results

Inability of a D2C with a Strong Linking Duplex to Undergo RCA

The conceptual cornerstone of the present application is the assumption that the components of a D2C with a strong linking duplex are unable to undergo RCA. To test this hypothesis, a D2C was synthesized (FIG. 1a) consisting of two component single-stranded DNA rings, named $^C$DNA$_i$ and r$^C$DNA$_{ii}$ (FIG. 1b; r stands for the single ribonucleotide, ribo-A, in the sequence of $^C$DNA$_{ii}$). Briefly, the linear DNA r$^L$DNA$_{ii}$ was circularized into r$^C$DNA$_{ii}$ using $^C$DNA$_i$ as the ligation template (sequences of all DNA species are provided in Table 1). The resultant D2C, denoted rD2C1, contains a strong linking duplex of 24 base pairs, which translate into 2 helical turns (boxed nucleotides in FIG. 1b). The reaction yield of rD2C1 was determined to be 58% (FIG. 1b).

Figure 2:
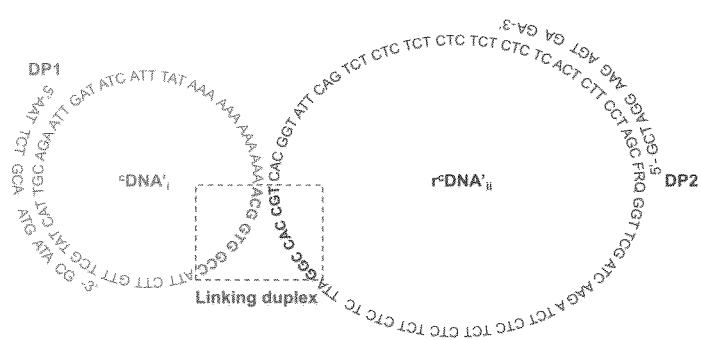
Figure 2:
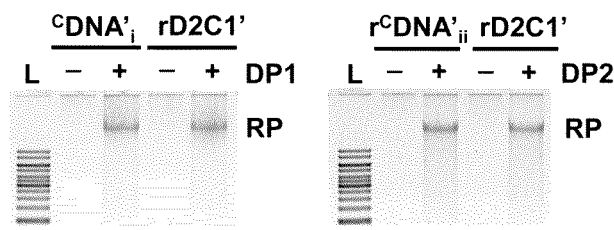

We then performed RCA reactions with gel-purified $^C$DNA$_i$, r$^C$DNA$_{ii}$, and rD2C1. Agarose gel analysis indicated that RCA products were produced with $^C$DNA$_i$ (using DP1 as the primer; FIG. 1c) and r$^C$DNA$_{ii}$ (using DP2 as the primer; FIG. 1c). In contrast, no RCA products were observed for rD2C1 using the same set of primers (FIG. 1c). This experiment shows that the topological constraint imposed by a strong linking duplex indeed prevents φ29 DNA polymerase (φ29DP) from replicating interlocked circular templates. In a control experiment, it was found that RCA was not inhibited when the linking duplex of the DNA catenane was made of 9 base-pairs (FIG. 2).

Enabling RCA Via Cleavage of a Component Ring by a DNAzyme

The inability of φ29DP to carry out RCA with topologically constrained DNA catenanes provides a novel avenue to explore these intricate DNA assemblies for practical applications. Next, the engineering of a highly unique biosensing system that takes advantage of topologically constrained DNA catenanes, DNAzymes and RCA was explored.

Figure 3:
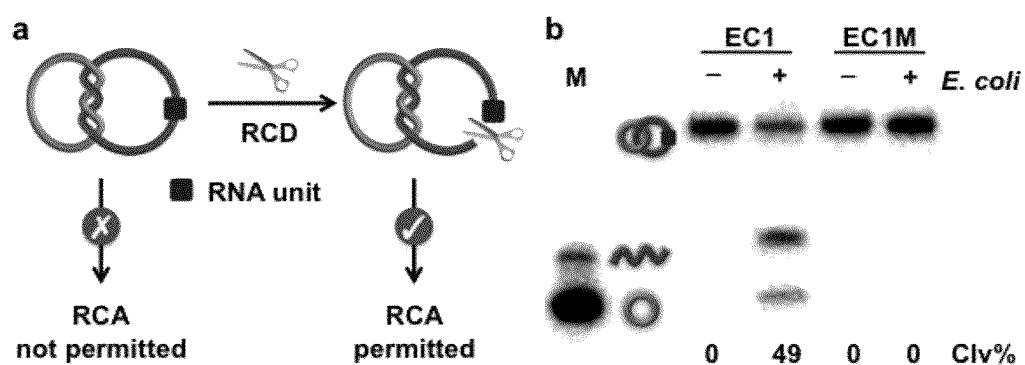

The principle of this biosensing system is shown in FIG. 3a. It uses an RNA-cleaving DNAzyme (RCD) to cleave the embedded RNA linkage within rD2C1 (note that the r$^C$D-NA$_{ii}$ was designed to contain a single ribonucleotide; see FIG. 1b). It is expected that the cleavage and linearization of r$^C$DNA$_{ii}$ by the RCD will release the topological constraint on the DNA assembly, which converts $^C$DNA$_i$ into a suitable template for RCA.

Figure 4:
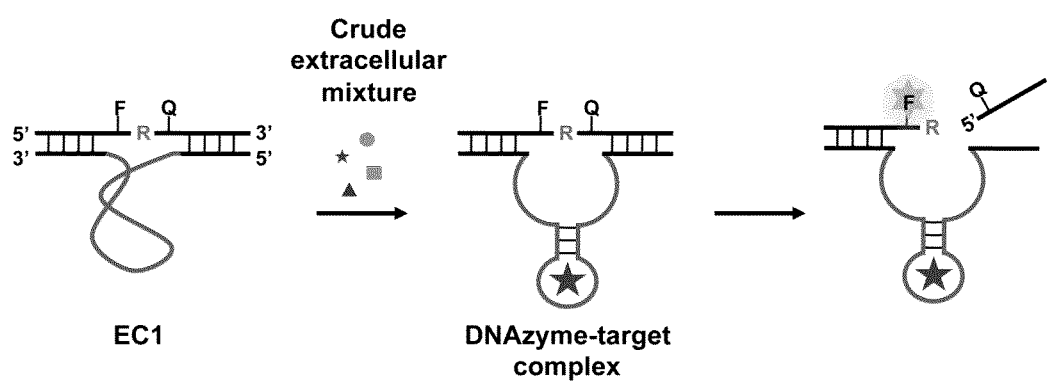
Figure 5:
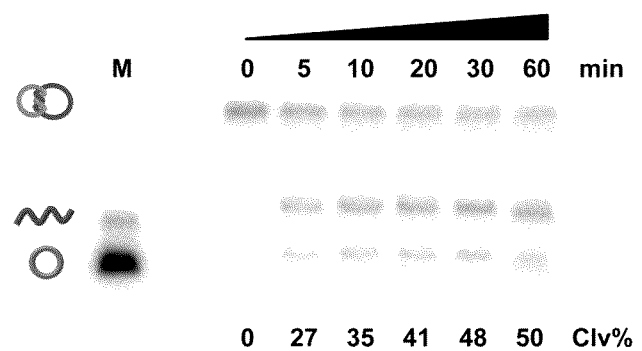

This approach should be compatible with any RNA-cleaving DNAzyme, making it a platform for detection of any species recognized by an allosteric DNAzyme. For this embodiment, EC1 was employed, which was previously isolated by from a random-sequence DNA pool using in vitro selection for specific detection of E. coli, a model bacterial pathogen [17,18]. EC1 was found to be activated by a protein molecule secreted specifically by E. coli cells (FIG. 4). Therefore, the use of EC1 enables the detection of this pathogen. As illustrated in FIG. 3b, EC1 was indeed able to cleave the r$^C$DNA$_{ii}$ present in rD2C1 in an E. coli-dependent manner, resulting in $^C$DNA$_i$ and a linear DNA$_{ii}$. An inactive DNAzyme mutant, EC1M, was also tested as a control. No cleavage product was observed for EC1M, indicating that the cleavage reaction is highly dependent on the DNAzyme sequence. The cleavage activity was also examined at different reaction times and found that the cleavage activity reached a plateau in 1 hour (FIG. 5). Thus, this reaction time was used for the remaining experiments.

Upon demonstrating EC1 mediated cleavage of r$^C$DNA$_{II}$ in rD2C1, the use of the cleavage reaction mixture was examined for initiating the RCA reaction with φ29DP. Because φ29DP has 3'-5' exonucleolytic activity that can degrade single-stranded DNA from the 3'-end but does not digest double-stranded DNA [19,20], the system should not require an external primer, as ϕ29DP should be able to convert the linearized $DNA_{ii}$ into a primer for RCA. To evaluate this hypothesis, the digestion of EC1-linerized $DNA_{ii}$ by ϕ29DP was explored. From the data presented in FIG. 6a, it is clear that ϕ29DP could not digest linearized $DNA_{ii}$ (comparing lanes 4 and 8).

Figure 6:
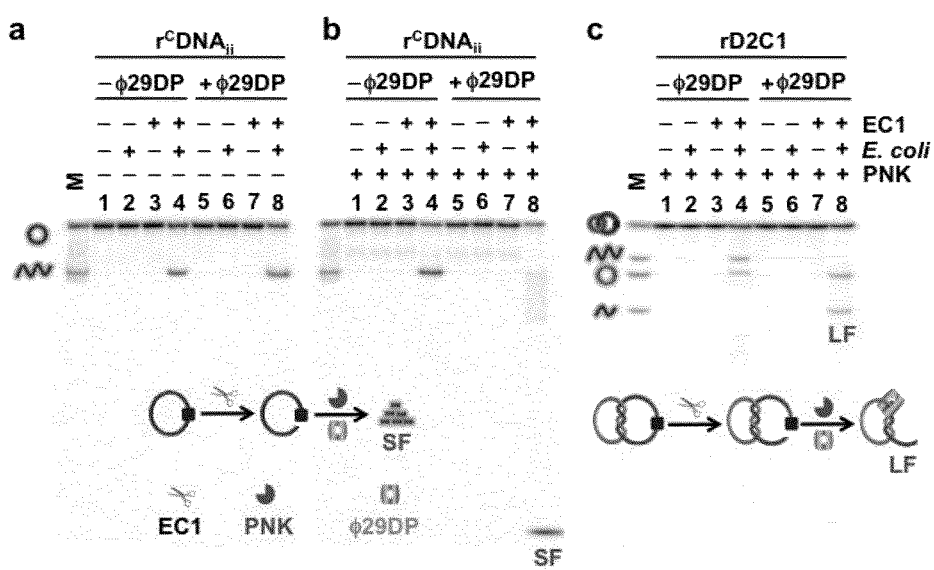
Figure 7:
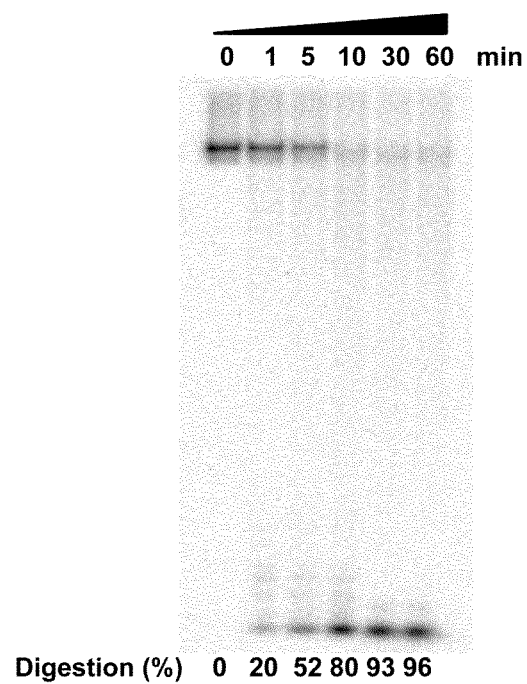

Without wishing to be bound by theory, there are two possible reasons for this finding. The first possibility is that ϕ29DP is incapable of digesting an RNA-terminated DNA molecule. However, testing with an RNA terminated oligonucleotide ruled out this possibility (FIG. 7). The second scenario is that ϕ29DP is not able to digest an RNA-terminated DNA molecule containing a 2',3'-cyclic phosphate on the RNA moiety, which is a common product of RNA cleavage [21]. To test the secondary scenario, the reaction mixture was treated with T4 polynucleotide kinase (PNK), which is known to be capable of removing the terminal 2',3'-cyclic phosphate in RNA [22]. As shown in FIG. 6b, treatment with PNK indeed facilitated the digestion of EC1-linearized $rDNA_{ii}$, as evidenced by the accumulation of small cleavage fragments (labeled SF in lane 8).

Figure 8:

The combined action of ϕ29DP and PNK was investigated on EC1-linearized $rDNA_{ii}$ within rD2C1. As shown in FIG. 6c, ϕ29DP degraded complexed $DNA_{ii}$ to a product of ~60 nt (labeled LF, representing long fragment; lane 8). The digestion assays were also conducted using different incubation times (FIG. 8). The progressive accumulation of LF and disappearance of the cleaved $rDNA_{ii}$ was observed. These experiments conclude that the combination of ϕ29DP and PNK can remove the single-stranded fragment at the 3'-end of the EC1-linearized $DNA_{ii}$ from rD2C1. It is expected that the trimmed $DNA_{ii}$ can now function as a primer to initiate RCA over the complexed $^CDNA_i$ template.

To verify the point above, the RCA reaction with the rD2C1 assembly was carried out. The reaction was performed in two sequential steps: activation of EC1 by E. coli and PNK treatment, followed by the addition of ϕ29DP and dNTPs. As expected, RCA products were indeed observed following this procedure (the last lane of FIG. 9a; the other lanes represent various controls). The RCA products were further analyzed through partial digestion with EcoRV (FIG. 10) as the sequence of $^CDNA_i$ was designed to contain a recognition sequence for this restriction enzyme. The appearance of the expected characteristic DNA banding pattern on the gel, which consists of monomeric, dimeric and other higher-ordered DNA amplicons, verified that the RCA products indeed contained the correct repetitive sequences.

Quantitative Detection of E. coli Using the DNA Catenane Sensor

Figure 9:
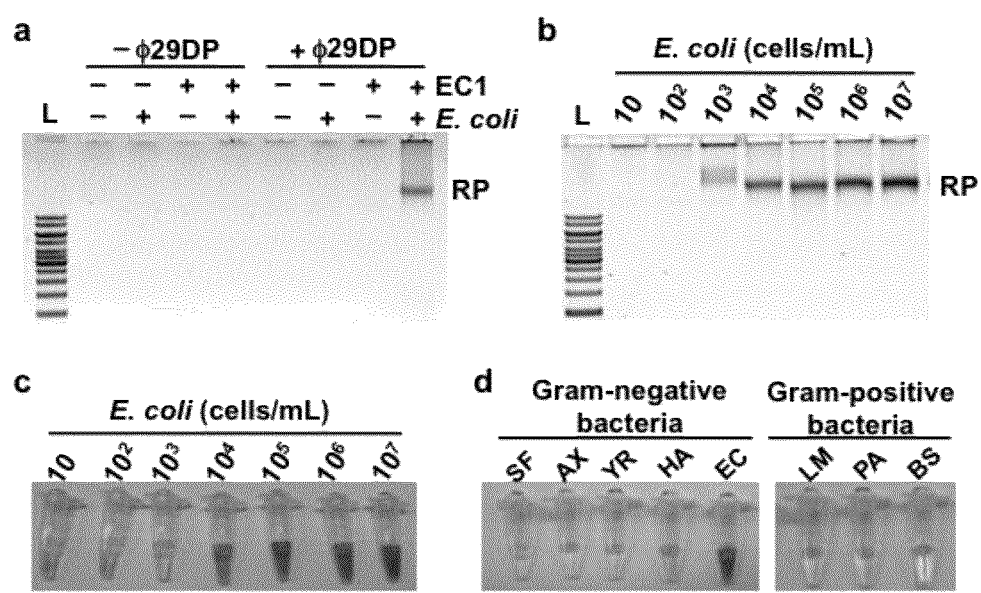
Figure 10:
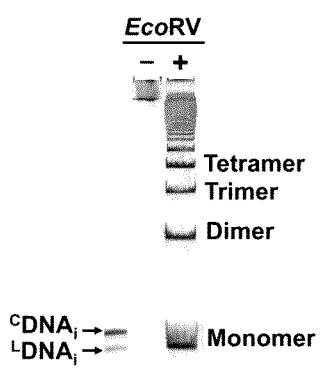

The feasibility of performing quantitative analysis using the DNA catenane sensor was next explored. Samples containing 10-$10^7$ E. coli cells $mL^{-1}$ were assessed for RCA amplified detection using a gel-staining method. By this method, detection as low as $10^3$ cells $mL^{-1}$ was possible (FIG. 9b). Although gel-based RP analysis can perform quantitative detection of E. coli, the procedure is extremely inconvenient. To overcome this issue, a colourimetric assay was developed by modifying the sequence of $^CDNA_i$ (the new sequence is named $^CDNA_iCD$) such that the RCA product contained a repetitive sequence of PW17, a peroxidase-like DNAzyme capable of generating a colourimetric signal [23-27]. In the presence of hemin, PW17 catalyzes the $H_2O_2$-mediated oxidation of 2,2'-azino-bis(3-ethylbenzthiazoline-6-sulphonic acid) (ABTS) into a coloured product.

As shown in FIG. 9c, this colourimetric method was indeed able to detect E. coli in a concentration-dependent manner and registered a detection sensitivity of $10^3$ cells $mL^{-1}$, similar to what was observed with the gel-based method.

The bacterial detection specificity was also evaluated using the colourimetric assay. Four other gram-negative and three gram-positive bacteria were selected that were previously tested for EC1-based detection. It was observed that none of these bacteria were able to produce a positive signal, indicating that the rD2C1/EC1 system retained the high recognition specificity for E. coli (FIG. 9d).

Figure 11:
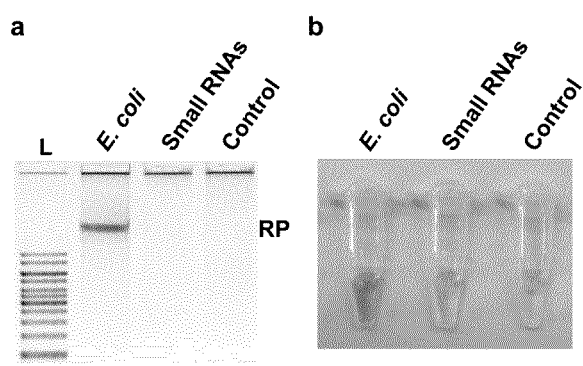

To further evaluate the specificity, the potential influence of small RNAs on E. coli detection were assessed because small RNAs (e.g., microRNA) are suitable primers for RCA. For this experiment, the total small RNAs extracted from breast cancer cell line MCF-7 were used. Agarose gel and colourimetric results indicated that the small RNAs were not able to induce the RCA reaction (FIG. 11). This high specificity is attributed to the unique topologically constrained structure of the DNA catenane.

Enhancing Detection Sensitivity Using Hyperbranched RCA

The possibility of performing a double-primed hyper-branched RCA (HRCA)[28] reaction was next explored with the rD2C1/EC1 system to further increase the detection sensitivity. In HRCA (FIG. 12a), multiple priming events can be continuously initiated by a forward primer (FP1) and a reverse primer (RP1) as the original RCA product strand elongates, resulting in an exponential amplification [29].

Figure 12:
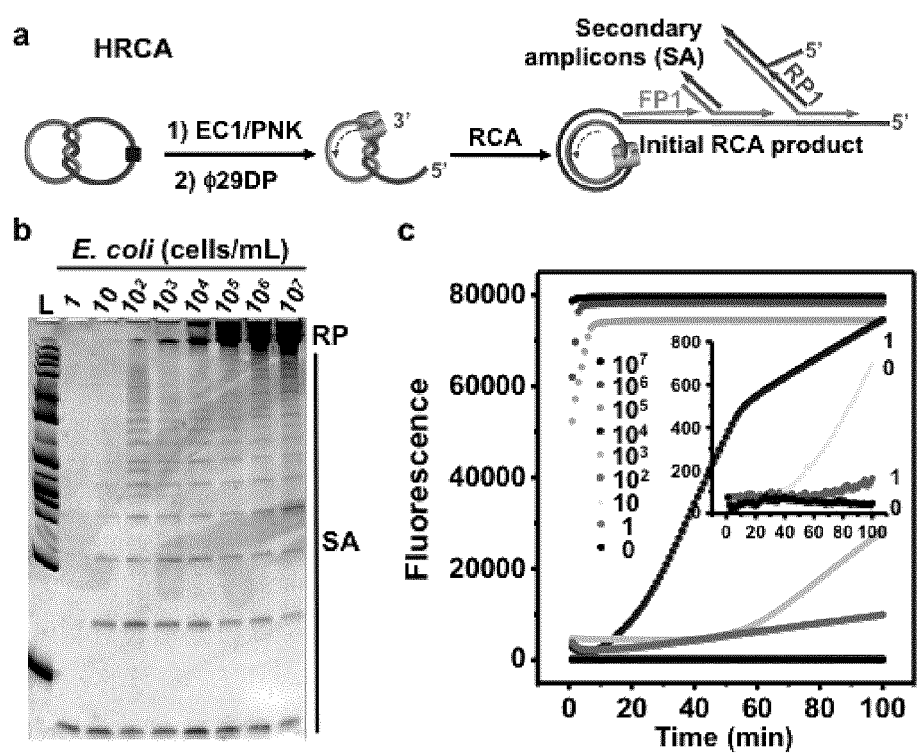

It was found that HRCA was indeed functional with the rD2C1/EC1 system: as shown in FIG. 12b, in addition to the observation of the RCA products on denaturing PAGE, a series of shorter DNA molecules were also produced, representing various secondary amplicons produced from the primary amplicons (i.e., initial RCA products). The HRCA reactions, in response to varying concentrations of E. coli, were also monitored in real time through the use of EvaGreen, a DNA-binding dye (FIG. 12c). It was found that this method exhibited much enhanced detection sensitivity, as it was able to detect E. coli at a concentration of as low as 10 cells $mL^{-1}$ without cell culture.

Figure 13:
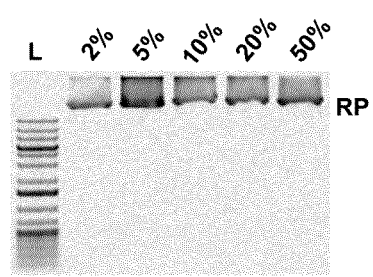
FIG. 13 shows the effect of blood on exemplary RCA reactions. RCA reactions of $^CDNA_i$ and DP1 were performed in the presence of 2, 5, 10, 20 and 50% human blood.
Figure 14:
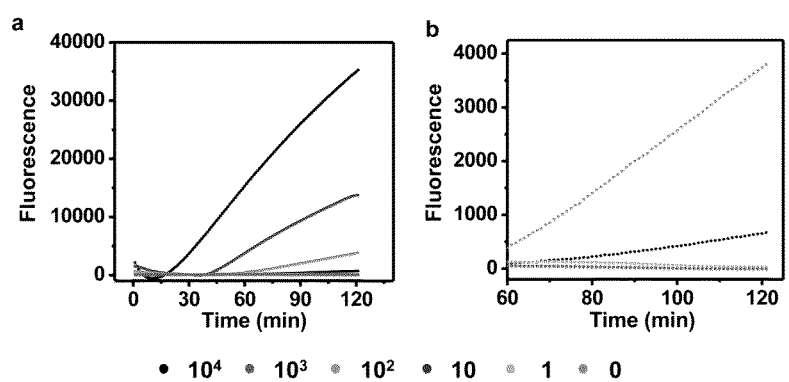
FIG. 14 shows exemplary E. coli-dependent HRCA reaction with human blood samples. Real-time monitoring of HRCA reactions with blood samples containing various concentrations of E. coli (cells mL$^{-1}$).

It is interesting to note that RCA reactions with ϕ29DP remain functional even in the presence of 50% human blood (FIG. 13). In comparison, PCR with Taq DNA polymerase was completely inhibited by less than 0.2% human blood [30-32]. To demonstrate the performance of the assay when using more complex samples, whole blood were spiked with E. coli and demonstrated that under these conditions the DNA catenane sensor was still able to detect E. coli at a concentration of 10 cells $mL^{-1}$ (FIG. 14). This observation is consistent with a recent report where EC1 was used to detect E. coli cells in human blood [33].

Figure 15:
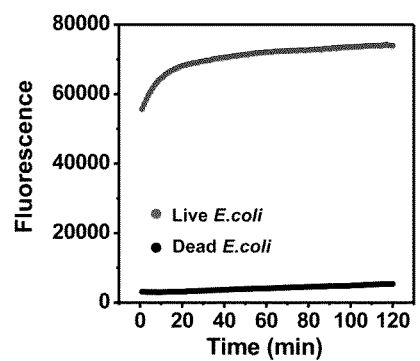
FIG. 15 shows an exemplary HRCA based detection of live E. coli cells and dead E. coli cells ($10^5$ cells mL$^{-1}$).

The ability of the DNA catenane sensor to distinguish between live and dead E. coli cells was also investigated. For this experiment, lysozyme was used to kill E. coli ($10^5$ cells $mL^{-1}$) and compared the signal responses of the catenane sensor in the presence of live and dead bacteria using HRCA. Negligible signal was observed with dead cells while a high activity was seen with live E. coli cells (FIG. 15).

Figure 16:
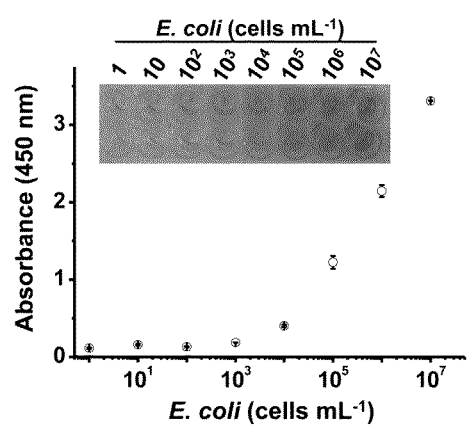
FIG. 16 shows the exemplary detection of E. coli using an ELISA kit.

An E. coli detection experiment was further performed with an enzyme-linked immunosorbent assay (ELISA) using a commercial ELISA kit designed to detect E. coli host cell protein (FIG. 16). It was found that the ELISA method was able to detect E. coli at a concentration of $10^3$ cells $mL^{-1}$. Therefore, the amplified DNA catenane sensor of the present application offers a detection sensitivity that is 100 times better than the ELISA method, while the test time for both methods are similar (˜3 hours; see Table 2 for additional information).

DISCUSSION

The examples demonstrate that mechanically interlocked DNA catenanes [2] with a strong linking duplex impose a significant topological constraint on their component DNA rings, making them unsuitable as the template for RCA. The embodiments demonstrate that such DNA nanostructures can be uniquely exploited for the design of a biosensing system where the elimination of the topological engagement, achieved simply through the cleavage of one interlocked nucleic acid ring in an analyte-dependent manner, frees up the other ring for the RCA reaction. As an example one of the two interlocked DNA rings was produced to contain a RNA linkage so that an RNA-cleaving DNAzyme can be used to cleave one interlocked ring. Through the use of an RNA-cleaving DNAzyme whose activity is specifically triggered by a secreted protein in E. coli, it has been shown that the featured biosensing system is capable of achieving ultra-sensitive detection of this bacterial pathogen.

The biosensing system featured in the present application offers some distinct advantages over existing detection methods for E. coli, such as cell culturing, PCR and ELISA (Table 2 for additional information). The use of RCA and HRCA for signal amplification makes this system extremely sensitive for bacterial detection, which can achieve the detection of as low as 10 cells mL$^{-1}$ without a cell-culturing step. The assay is also more compatible with point-of-care or field applications because RCA is an isothermal process and there is no need for DNA extraction (as in the case of PCR). In addition, the system functions well with biological samples (no interferences from small RNAs and compatibility with blood samples).

The same design may be extended to other RNA-cleaving DNAzymes, DNA-cleaving DNAzymes, as well as ribozymes and protein enzymes that have DNA or RNA cleaving activities. Although rolling circle amplification was exploited to achieve signal amplification in this study, it should be feasible to take advantage of other signal amplification strategies, such as the DNAzyme cross-amplification system developed by Levy and Ellington that does not need a DNA polymerase [34]. The concept presented in this application provides opportunities for exploring mechanically interlocked DNA architectures for many potential applications in chemical biology, medical diagnostics, and environmental monitoring.

While the present application has been described with reference to examples, it is to be understood that the scope of the claims should not be limited by the embodiments set forth in the examples, but should be given the broadest interpretation consistent with the description as a whole.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

TABLE 1

| Sequences of oligonucleotides |  |
| --- | --- |
| Synthesis of $^C$DNA$_i$: $^C$DNA$_i$ is made via circularization of $^L$DNA$_i$ in the presence of DNA$_i$CT as the template | |
| $^L$DNA$_i$ | ACTGTAACCA TTCTTGTTTC GTATCATTGC AGAATTGATA TCATTTATCT GAATACCGTG (SEQ ID NO: 1) |
| DNA$_i$CT | GTTACAGTCA CGGTAT (SEQ ID NO: 2) |
| Synthesis of $^C$DNA$_i$CD: $^C$DNA$_i$CD is made via circularization of $^L$DNA$_i$CD in the presence of DNA$_i$CT as the template | |
| $^L$DNA$_i$CD | ACTGTAACCA TTAAACCCAA CCCGCCCTAC CCAAAAGATA TCATTTATCT GAATACCGTG (SEQ ID NO: 3) |
| Synthesis of $^C$DNA'$_i$: $^C$DNA'$_i$ is made via circularization of $^L$DNA'$_i$ in the presence of DNA'$_i$CT as the template | |
| $^L$DNA'$_i$ | TGCAGAATTG ATATCATTTA TAAAAAAAAA AAAACGGTGG CCATTCTTGT TTCGTATCAT (SEQ ID NO: 4) |
| DNA'$_i$CT | AATTCTGCAA TGATACG (SEQ ID NO: 5) |
| Synthesis of r$^L$DNA$_{ii}$: r$^L$DNA$_{ii}$ is produced via ligating FS28, DNA$_{ii}$F1 and DNA$_{ii}$F2 in the presence of DNA$_{ii}$T1 and DNA$_{ii}$T2 as ligation templates | |
| FS28 | ACTCTTCCTA GCFRQGGTTC GATCAAGA (SEQ ID NO: 6) |
| DNA$_{ii}$F1 | CACGGTATTC AGTCTCTCTC TCTCTCTCT CTC (SEQ ID NO: 7) |
| DNA$_{ii}$F2 | TCTCTCTCTC TCTCTCTCTC AATGGTTAC AGT (SEQ ID NO: 8) |
| DNA$_{ii}$T1 | TAGGAAGAGT GAGAGAGA (SEQ ID NO: 9) |

TABLE 1 -continued

Sequences of oligonucleotides

| | |
|---|---|
| DNA$_{ii}$T2 | GAGAGAGAGA TCTTGATCG A (SEQ ID NO: 10) |

Synthesis of r$^C$DNA$_{ii}$: r$^C$DNA$_{ii}$ is made via circularization of r$^L$DNA$_{ii}$ in the presence of DNA$_{ii}$CT as the template

| | |
|---|---|
| DNA$_{ii}$CT | GAATACCGTG ACTGTAACC A (SEQ ID NO: 11) |

Synthesis of r$^L$DNA'$_{ii}$: r$^L$DNA'$_{ii}$ is produced via ligating FS28, DNA$_{ii}$F1 and DNA$_{ii}$F2' in the presence of DNA$_{ii}$T1 and DNA$_{ii}$T2 as ligation templates

| | |
|---|---|
| DNA$_{ii}$F2' | TCTCTCTCTC TCTCTCTCTC TTAGGCCAC CGT (SEQ ID NO: 12) |

Synthesis of r$^C$DNA'$_{ii}$: r$^C$DNA$_{ii}$ is made via circularization of r$^L$DNA'$_{ii}$ in the presence of DNA'$_{ii}$CT as the template

| | |
|---|---|
| DNA'$_{ii}$CT | GAATACCGTG ACGGTGGCCT (SEQ ID NO: 13) |

E. coil-responsive DNAzyme EC1 and its inactive mutant EC1M

| | |
|---|---|
| EC1 (X = Inverted dT) | GATGTGCGTT GTCGAGACCT GCGACCGGAA CACTACACTG TGTGGGGATG GATTTCTTTA CAGTTGTGTG X (SEQ ID NO: 14) |
| EC1M (X = Inverted dT) | GATGTGCGTA AAGCTCACCT GCGACCGGAA CACTACTGAC ACTGGGGATG GATTTCTTTA CAGTTGTGTG X (SEQ ID NO: 15) |

DNA primers for RCA

| | |
|---|---|
| DP1 | AATTCTGCAA TGATACG (SEQ ID NO: 16) |
| DP2 | GCTAGGAAGA GTGAGA (SEQ ID NO: 17) |

DNA primers for HRCA

| | |
|---|---|
| FP1 | GTTACAGTCA CGGTAT (SEQ ID NO: 18) |
| RP1 | CATTGCAGAA TTGATA (SEQ ID NO: 19) |

DNA template for restriction digestion

| | |
|---|---|
| DT1 | CAGAATTGAT ATCATTTATCTG (SEQ ID NO: 20) |

TABLE 2

Major advantages of our method in comparison with the traditional microbial detection system, a PCR test and ELISA for bacterium detection.

| Method | Test time | Sensitivity |
|---|---|---|
| Roche Septifast[a] | 6.7 hours (lysis 15 minutes; DNA extraction 90 minutes; DNA amplification 150 minutes; data analysis 30 minutes) | 10-100 cells mL$^{-1}$ |
| Biomerieux (BacT/ALERT ® FA)[b] | 12.0-43.9 hours (culture) for 10 cells per bottle or less; 10.8-35.2 hours for 100 cells per bottle or less | 10-100 cells mL$^{-1}$ |
| ELISA[c] | 3 hours (set-up 15 minutes; 1$^{st}$ incubation 60 min; 1st washing 10 min (5 washes); 2$^{nd}$ incubation 60 min; 2$^{nd}$ washing 10 min (5 washes); substrate incubation 15 min; stop step and data reading 10 min) | 10$^3$ cells mL$^{-1}$ |
| Our method | 2.3 hours (sample preparation 18 minutes; DNAzyme 60 minutes; PNK/RCA 60 minutes) | 10 cells mL$^{-1}$ |

FULL CITATION FOR DOCUMENTS REFERRED TO IN THE APPLICATION

1. Mao, C., Sun, W. & Seeman, N. C. Assembly of Borromean rings from DNA. *Nature* 386, 137-138 (1997).
2. Wang, H., Du, S. M. & Seeman, N. C. Tight single-stranded DNA knots. *J. Biomol. Struct. Dyn.* 10, 853-863 (1993).
3. Schmidt, T. L. & Heckel, A. Construction of a structurally defined double-stranded DNA catenane. *Nano Lett.* 11, 1739-1742 (2011).
4. Ackermann, D., Schmidt, T. L., Hannam, J. S., Purohit, C. S., Heckel, A. & Famulok, M. A double-stranded DNA rotaxane. *Nat. Nanotechnol.* 5, 436-442 (2010).
5. Zhang, F., Nangreave, J., Liu, Y. & Yan, H. Structural DNA nanotechnology: state of the art and future perspective. *J. Am. Chem. Soc.* 136, 11198-11211 (2014).
6. Chen, Y. J., Groves, B., Muscat, R. A. & Seelig, G. DNA nanotechnology from the test tube to the cell. *Nat. Nanotechnol.* 10, 748-760 (2015).
7. Pinheiro, A. V., Han, D., Shih, W. M. & Yan, H. Challenges and opportunities for structural DNA nanotechnology. *Nat. Nanotechnol.* 6, 763-772 (2011).
8. Elbaz, J., Cecconello, A., Fan, Z., Govorov, A. O. & Willner, I. Powering the programmed nanostructure and function of gold nanoparticles with catenated DNA machines. *Nat. Commun.* 4, 2000 (2013).
9. Liu, X. Q., Lu, C. H. & Willner, I. Switchable reconfiguration of nucleic acid nanostructures by stimuli-responsive DNA machines. *Acc. Chem. Res.* 47, 1673-1680 (2014).
10. Li, T., Lohmann, F. & Famulok, M. Interlocked DNA nanostructures controlled by a reversible logic circuit. *Nat. Commun.* 5, 4940 (2013).
11. Schmidt, T. L. & Heckel, A. Construction of a structurally defined double-stranded DNA catenane. *Nano Lett.* 11, 1739-1742 (2011).
12. Zhang, D. Y. & G. seelig. Dynamic DNA nanotechnology using strand-displacement reactions. *Nat. Chem.* 3, 103-113 (2011).
13. Wu, Z. S., Shen, Z., Tram, K. & Li, Y. Engineering interlocking DNA rings with weak physical interactions. *Nat. Commun.* 5, 4279 (2014).
14. Fire, A. & Xu, S. Q. Rolling replication of short DNA circles. *Proc. Natl. Acad. Sci. USA* 92, 4641-4645 (1995).
15. Liu, D., Daubendiek, S. L., Zillman, M. A., Ryan, K. & Kool, E. T. Rolling circle DNA synthesis: small circular oligonucleotides as efficient templates for DNA polymerases. *J. Am. Chem. Soc.* 118, 1587-1594 (1996).
16. Zhao, W., Ali, M. M., Brook, M. A. & Li, Y. Rolling circle amplification: applications in nanotechnology and biodetection with functional nucleic acids. *Angew. Chem., Int. Ed.* 47, 6330-6337 (2008).
17. Ali, M. M., Aguirre, S. D., Lazim, H. & Li, Y. Fluorogenic DNAzyme probes as bacterial indicators. *Angew. Chem. Int. Ed.* 50, 3751-3754 (2011).
18. Aguirre, S. D., Ali, M. M., Salena, B. J. & Li, Y. A sensitive DNA enzyme-based fluorescent assay for bacterial detection. *Biomolecules* 3, 563-577 (2013).
19. Liu, M., Zhang, W., Zhang, Q., Brennan, J. D. & Li, Y. Biosensing by tandem reactions of structure switching, nucleolytic digestion, and DNA amplification of a DNA assembly. *Angew. Chem. Int. Ed.* 54, 9637-9641 (2015).
20. Blanco, L. & Salas, M. Characterization of a 3' 5' exonuclease activity in the phage 429-encoded DNA polymerase. *Nucleic Acids Res.* 13, 1239-1249 (1985).
21. Silverman, S. K. In vitro selection, characterization, and application of deoxyribozymes that cleave RNA. *Nucleic Acids Res.* 33, 6151-6163 (2015).
22. Schurer, H., Lang, K., Schuster, J. & Morl, M. A universal method to produce in vitro transcripts with homogeneous 3' ends. *Nucleic Acids Res.* 30, e56 (2002).
23. Li, Y. & Sen, D. A catalytic DNA for porphyrin metallation. *Nat. Struct. Biol.* 3, 743-747 (1996).
24. Travascio, P., Li, Y. & Sen, D. DNA-enhanced peroxidase activity of a DNA aptamer-hemin complex. *Chem. Biol.* 5, 505-517 (1998).
25. Travascio, P., Witting, P. K., Mauk, A. G. & Sen, D. The peroxidase activity of a hemin-DNA oligonucleotide complex: free radical damage to specific guanine bases of the DNA. *J. Am. Chem. Soc.* 123, 1337-1348 (2001).
26. Cheglakov, Z., Weizmann, Y., Basnar, B. & Willner, I. Diagnosing viruses by the rolling circle amplified synthesis of DNAzymes. *Org. Biomol. Chem.* 5, 223-225 (2007).
27. Tian, Y., He, Y. & Mao, C. Cascade signal amplification for DNA detection. *ChemBioChem* 7, 1862-1864 (2006).
28. Zhang, D., Brandwein, M., Hsuih, T. & Li, H. Amplification of target-specific, ligation-dependent circular probe. *Gene* 211, 277-285 (1998).
29. Lizardi, P. M., Huang, X., Zhu, Z., Bray-Ward, P., Thomas, D. C. & Ward, D. C. Mutation detection and single-molecule counting using isothermal rolling-circle amplification. *Nat. Genet.* 19, 225-232 (1998).
30. Al-Soud, W. A. & Radstrom, P. Effect of amplification facilitators on diagnostic PCR in the presence of blood, feces and meat. *J. Clin. Microbiol.* 38, 4463-4470 (2000).
31. Al-Soud, A. W. & Radstrom, P. Capacity of nine thermostable DNA polymerases to mediate DNA amplification in the presence of PCR-inhibiting samples. *Appl. Environ. Microbiol.* 64, 3748-3753 (1998).
32. Schrader, C., Schielke, A., Ellerbroek, L. & Johne, R. PCR inhibitors-occurrence, properties and removal. *J. Appl. Microbiol.* 113, 1014-1026 (2012).
33. Kang, D. K., Ali, M. M., Zhang, K., Huang, S. S., Peterson, E., Digman, M. A., Gratton, E. & Zhao, W. Rapid detection of single bacteria in unprocessed blood using Integrated Comprehensive Droplet Digital Detection. *Nat. Commun.* 5, 5427 (2014).
34. Levy, M. & Ellington, A. D. Exponential growth by cross-catalytic cleavage of deoxyribozymogens. *Proc. Natl. Acad. Sci. USA.* 100, 6416-6421 (2003).

The invention claimed is:

1. A biosensor for detection of a microorganism target comprising:
   a) a first single-stranded nucleic acid ring comprising a linkage that is cleaved by an enzyme from the microorganism target or by an enzyme that is activated by a molecule from the microorganism; and
   b) a second single-stranded nucleic acid ring comprising a sequence complementary to a region of the first single-stranded nucleic acid ring,
wherein the first and second single-stranded nucleic acid rings form a nucleic acid catenane structure with a linking duplex.

2. The biosensor of claim 1, wherein the linkage is cleaved by an RNA-cleaving DNAzyme, a DNA-cleaving DNAzyme, a ribozyme or a protein enzyme that has DNA and/or RNA cleaving activities activated by a molecule from the microorganism target.

3. The biosensor of claim 2, wherein the linkage is cleaved by an RNA-cleaving DNAzyme that is activated by a molecule from the microorganism target.

4. The biosensor of claim 1, wherein the linkage is cleaved by an allosteric DNAzyme, ribozyme or protein enzyme that is activated by an activator molecule in a sample containing the microorganism target prior to cleaving the linkage.

5. The biosensor of claim 1, wherein the first single-stranded nucleic acid ring is a single stranded DNA ring comprising a single ribonucleotide linkage and the second single-stranded nucleic acid ring is a single stranded DNA ring comprising a sequence that is complementary to a region of the first single-stranded DNA ring.

6. The biosensor of claim 5, wherein the sequence in the first single-stranded DNA ring that is complementary to a region of the first single-stranded DNA ring comprises from 6 to 50 nucleotides.

7. The biosensor of claim 1, further comprising the enzyme that is activated by a molecule from the microorganism.

8. The biosensor of claim 1, further comprising reagents for performing RCA.

9. The biosensor of claim 8, wherein the reagents for performing RCA further comprise forward and reverse primers for performing hyperbranched RCA (HRCA).

10. The biosensor of claim 1, wherein the first and second nucleic acid rings are comprised of DNA, with the first nucleic acid ring comprising a single ribonucleotide linkage.

11. The biosensor of claim 1, wherein detection of the microorganism target is performed by detection of RCA products (RP) and the biosensor further comprises one or more reporter molecules for detection of the RP.

12. The biosensor of claim 11, wherein the one or more reporter molecules for detection of the RP comprise a detection system selected from a fluorescent system, a colorimetric system, a radiolabeled system and an electrochemical system.

13. The biosensor of claim 11, wherein the one or more reporter molecules are incorporated in the reagents for performing RCA and/or first and/or second single-stranded nucleic acid rings.

14. The biosensor of claim 11, wherein the first single-stranded nucleic acid ring is modified to produce an RP containing repetitive units of a peroxidase-mimicking DNAzyme, PW17, generating a detectable colorimetric signal and hemin, $H_2O_2$ and 2,2'azine-bis(3-ethylbenzthiasoline-6-sulfonic acid (ABTS) are included in the reagents for performing RCA.

15. The biosensor of claim 1 having a detection sensitivity of from about 10 cells/m L to about 1000 cells/ml.

16. A microorganism detection kit comprising a biosensor of claim 1 and optionally reagents for performing an assay using the biosensor and/or instructions for using the biosensor in the assay and any controls needed to perform the assay.

17. A method of detecting a microorganism target in a sample comprising exposing the sample to the biosensor of claim 1, wherein an enzyme from the microorganism target cleaves the linkage in the first single-stranded nucleic acid ring, allowing rolling-circle amplification to occur and detection of rolling circle amplification products indicates the presence of the microorganism in the sample.

18. The method of claim 17, wherein cleavage of the linkage results in release and linearization of first single-stranded nucleic acid and the linearized first single-stranded nucleic acid then acts as a primer for rolling circle amplification (RCA), the second single-stranded nucleic acid ring acts as the circular template for RCA, and detection of RCA products (RP) indicates the presence of the microorganism target.

19. The method of claim 17, wherein cleavage of the linkage results in release and linearization of first single-stranded nucleic acid and the second single-stranded nucleic acid ring acts as the circular template for RCA, and detection of RCA products (RP) indicates the presence of the microorganism target.

20. The method of claim 17, wherein the RCA products are detected using an electrophoresis system.

* * * * *

SEQUENCE LISTING

```
<160> NUMBER OF SEQ ID NOS: 20

<210> SEQ ID NO 1
<211> LENGTH: 60
<212> TYPE: DNA
<213> ORGANISM: Artificial Sequence
<220> FEATURE:
```

```
<223> OTHER INFORMATION: Synthetic Construct

<400> SEQUENCE: 1
actgtaacca ttcttgtttc gtatcattgc agaattgata tcatttatct gaataccgtg    60

<210> SEQ ID NO 2
<211> LENGTH: 16
<212> TYPE: DNA
<213> ORGANISM: Artificial Sequence
<220> FEATURE:
<223> OTHER INFORMATION: Synthetic Construct

<400> SEQUENCE: 2
gttacagtca cggtat                                                    16

<210> SEQ ID NO 3
<211> LENGTH: 60
<212> TYPE: DNA
<213> ORGANISM: Artificial Sequence
<220> FEATURE:
<223> OTHER INFORMATION: Synthetic Construct

<400> SEQUENCE: 3
actgtaacca ttaaacccaa cccgccctac ccaaaagata tcatttatct gaataccgtg    60

<210> SEQ ID NO 4
<211> LENGTH: 60
<212> TYPE: DNA
<213> ORGANISM: Artificial Sequence
<220> FEATURE:
<223> OTHER INFORMATION: Synthetic Construct

<400> SEQUENCE: 4
tgcagaattg atatcattta taaaaaaaaa aaaacggtgg ccattcttgt ttcgtatcat    60

<210> SEQ ID NO 5
<211> LENGTH: 17
<212> TYPE: DNA
<213> ORGANISM: Artificial Sequence
<220> FEATURE:
<223> OTHER INFORMATION: Synthetic Construct

<400> SEQUENCE: 5
aattctgcaa tgatacg                                                   17

<210> SEQ ID NO 6
<211> LENGTH: 28
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (13)..(13)
<223> OTHER INFORMATION: n is fluorescein-dT
<220> FEATURE:
<221> NAME/KEY: misc_feature
<222> LOCATION: (14)..(14)
<223> OTHER INFORMATION: n is adenosine ribonucleotide
<220> FEATURE:
<221> NAME/KEY: misc_feature
<222> LOCATION: (15)..(15)
<223> OTHER INFORMATION: n is dabcyl-dT

<400> SEQUENCE: 6
actcttccta gcnnnggttc gatcaaga                                       28
```

```
<210> SEQ ID NO 7
<211> LENGTH: 32
<212> TYPE: DNA
<213> ORGANISM: Artificial Sequence
<220> FEATURE:
<223> OTHER INFORMATION: Synthetic Construct

<400> SEQUENCE: 7
cacggtattc agtctctctc tctctctctc tc                                        32

<210> SEQ ID NO 8
<211> LENGTH: 32
<212> TYPE: DNA
<213> ORGANISM: Artificial Sequence
<220> FEATURE:
<223> OTHER INFORMATION: Synthetic Construct

<400> SEQUENCE: 8
tctctctctc tctctctctc aatggttaca gt                                        32

<210> SEQ ID NO 9
<211> LENGTH: 18
<212> TYPE: DNA
<213> ORGANISM: Artificial Sequence
<220> FEATURE:
<223> OTHER INFORMATION: Synthetic Construct

<400> SEQUENCE: 9
taggaagagt gagagaga                                                        18

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
gagagagaga tcttgatcga                                                      20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
gaataccgtg actgtaacca                                                      20

<210> SEQ ID NO 12
<211> LENGTH: 32
<212> TYPE: DNA
<213> ORGANISM: Artificial Sequence
<220> FEATURE:
<223> OTHER INFORMATION: Synthetic Construct

<400> SEQUENCE: 12
tctctctctc tctctctctc ttaggccacc gt                                        32

<210> SEQ ID NO 13
<211> LENGTH: 20
<212> TYPE: DNA
<213> ORGANISM: Artificial Sequence
<220> FEATURE:
<223> OTHER INFORMATION: Synthetic Construct
```

```
<400> SEQUENCE: 13
gaataccgtg acggtggcct                                              20

<210> SEQ ID NO 14
<211> LENGTH: 71
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (71)..(71)
<223> OTHER INFORMATION: n is inverted dt

<400> SEQUENCE: 14
gatgtgcgtt gtcgagacct gcgaccggaa cactacactg tgtggggatg gatttctttta    60 cagttgtgtg n                                                       71

<210> SEQ ID NO 15
<211> LENGTH: 71
<212> TYPE: DNA
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (71)..(71)
<223> OTHER INFORMATION: n is inverted dt

<400> SEQUENCE: 15
gatgtgcgta aagctcacct gcgaccggaa cactactgac actggggatg gatttctttta    60 cagttgtgtg n                                                       71

<210> SEQ ID NO 16
<211> LENGTH: 17
<212> TYPE: DNA
<213> ORGANISM: Artificial Sequence
<220> FEATURE:
<223> OTHER INFORMATION: Synthetic Construct

<400> SEQUENCE: 16
aattctgcaa tgatacg                                                 17

<210> SEQ ID NO 17
<211> LENGTH: 16
<212> TYPE: DNA
<213> ORGANISM: Artificial Sequence
<220> FEATURE:
<223> OTHER INFORMATION: Synthetic Construct

<400> SEQUENCE: 17
gctaggaaga gtgaga                                                  16

<210> SEQ ID NO 18
<211> LENGTH: 16
<212> TYPE: DNA
<213> ORGANISM: Artificial Sequence
<220> FEATURE:
<223> OTHER INFORMATION: Synthetic Construct

<400> SEQUENCE: 18
gttacagtca cggtat                                                  16

<210> SEQ ID NO 19
<211> LENGTH: 16
```

```
<212> TYPE: DNA
<213> ORGANISM: Artificial Sequence
<220> FEATURE:
<223> OTHER INFORMATION: Synthetic Construct

<400> SEQUENCE: 19
cattgcagaa ttgata                                              16

<210> SEQ ID NO 20
<211> LENGTH: 22
<212> TYPE: DNA
<213> ORGANISM: Artificial Sequence
<220> FEATURE:
<223> OTHER INFORMATION: Synthetic Construct

<400> SEQUENCE: 20
cagaattgat atcatttatc tg                                       22
```